United States Patent
Hong et al.

(10) Patent No.: US 12,268,781 B2
(45) Date of Patent: Apr. 8, 2025

(54) SUSTAINED-RELEASE PHARMACEUTICAL COMPOSITIONS COMPRISING A THERAPEUTIC AGENT FOR TREATING DEMENTIA AND USES THEREOF

(71) Applicants: TAIWAN LIPOSOME CO., LTD., Taipei (TW); TLC BIOPHARMACEUTICALS, INC., South San Francisco, CA (US)

(72) Inventors: Keelung Hong, South San Francisco, CA (US); Hao-Wen Kao, South San Francisco, CA (US); Yi-Yu Lin, South San Francisco, CA (US); Walter Gwathney, South San Francisco, CA (US)

(73) Assignees: TAIWAN LIPOSOME CO., LTD., Taipei (TW); TLC BIOPHARMACEUTICALS, INC., South San Francisco, CA (US)

(*) Notice: Subject to any disclaimer, the term of this patent is extended or adjusted under 35 U.S.C. 154(b) by 961 days.

(21) Appl. No.: 17/262,300

(22) PCT Filed: Jul. 23, 2019

(86) PCT No.: PCT/US2019/042933
§ 371 (c)(1),
(2) Date: Jan. 22, 2021

(87) PCT Pub. No.: WO2020/023445
PCT Pub. Date: Jan. 30, 2020

(65) Prior Publication Data
US 2021/0378961 A1 Dec. 9, 2021

Related U.S. Application Data

(60) Provisional application No. 62/702,563, filed on Jul. 24, 2018.

(51) Int. Cl.
*A61K 9/127* (2006.01)
*A61K 9/1271* (2025.01)
*A61K 31/13* (2006.01)
*A61K 31/27* (2006.01)
*A61K 47/02* (2006.01)
*A61K 47/26* (2006.01)
*A61K 47/28* (2006.01)

(52) U.S. Cl.
CPC ............ *A61K 9/1271* (2013.01); *A61K 31/13* (2013.01); *A61K 31/27* (2013.01); *A61K 47/02* (2013.01); *A61K 47/26* (2013.01); *A61K 47/28* (2013.01)

(58) Field of Classification Search
CPC ...... A61K 9/1271; A61K 31/13; A61K 31/27; A61K 47/02; A61K 47/26; A61K 47/28; A61K 9/1278; A61K 31/55; A61K 9/0019; A61K 31/445; A61P 25/28
See application file for complete search history.

(56) References Cited

U.S. PATENT DOCUMENTS

| | | | |
|---|---|---|---|
| 9,737,485 B2 | 8/2017 | Hayes | |
| 9,877,918 B2 | 1/2018 | Yamashita | |
| 2007/0116753 A1 | 5/2007 | Hong et al. | |
| 2007/0275048 A1 | 11/2007 | Liu et al. | |
| 2008/0031935 A1* | 2/2008 | Bodenteich | A61K 9/127 514/297 |
| 2013/0202686 A1* | 8/2013 | Yamashita | A61K 9/127 424/450 |
| 2013/0224287 A1 | 8/2013 | Reis et al. | |
| 2013/0309297 A1 | 11/2013 | Yamashita et al. | |
| 2014/0220110 A1 | 8/2014 | Hayes et al. | |
| 2017/0266295 A1* | 9/2017 | Kan | A61K 31/704 |

FOREIGN PATENT DOCUMENTS

| | | |
|---|---|---|
| CN | 101601654 A | 12/2009 |
| CN | 102406606 A | 4/2012 |
| CN | 103189050 A | 7/2013 |
| CN | 103370055 A | 10/2013 |
| CN | 103370055 | 6/2015 |
| CN | 105163720 A | 12/2015 |
| CN | 107260680 A | 10/2017 |
| CN | 105163720 | 10/2019 |
| TW | 200605908 A | 2/2006 |
| WO | 2014121211 A2 | 8/2014 |
| WO | 2014121235 A2 | 8/2014 |

OTHER PUBLICATIONS

El-Helaly et al. (Electrosteric stealth Rivastigmine loaded liposomes for brain targeting. Drug Delivery, 2017). (Year: 2017).*
Yang (Enhanced brain distribution and pharmacodynamics of rivastigmine by liposomes following intranasal administration, International Journal of Pharmaceutics, 2013 (Year: 2013).*
Sara Nageeb El-Helaly et al. "Electrosteric Stealth Rivastigmine Loaded Lipsomes for Brain Targeting: Preparation, Characterization, Ex-Vivo, Bio-Distribution and In Vivo Pharmacokinetic Studies," Drug Delivery, Jan. 2017, pp. 692-700, vol. 24, No. 1.

(Continued)

*Primary Examiner* — Robert A Wax
*Assistant Examiner* — John Seungjai Kwon
(74) *Attorney, Agent, or Firm* — Piloff Passino & Cosenza LLP; Rachel Piloff; Sean Passino

(57) ABSTRACT

The present invention relates to pharmaceutical compositions comprising at least one liposome and a therapeutic agent for treating dementia with a high drug to lipid ratio and a high encapsulation efficiency. The pharmaceutical composition improves the pharmacokinetic profile and sustains the release of the therapeutic agent. Also provided is the method for treating dementia using the pharmaceutical composition disclosed herein.

15 Claims, 3 Drawing Sheets

(56) References Cited

OTHER PUBLICATIONS

International Search Report & Written Opinion for PCT/US2019/042933, mailed Oct. 7, 2019.
Zhen-Zhen Yang et al., "Enhanced brain distribution and pharmacodynamics of rivastigmine by liposomes following intranasal administration." International Journal of Pharmaceutics, Jan. 2013, pp. 344-354, vol. 452.
Office Action for related Taiwan application, mailed Jul. 7, 2020.
Office Action for related Taiwan application, mailed Nov. 26, 2020.
Jun Chen et al., "Preparation and pharmacokinetic investigation of propranolol-loaded elastic liposomes composed of DP-PC and SPC," Chinese Pharmaceutical Journal, Oct. 22, 2013, pp. 1,761-1,765, vol. 48, No. 20.
Zhen-Zhen Yang et al., "Preparation of rivastigmine liposome and its pharmacokinetics in rats after intranasal administration," Acta Pharmaceutica Sinica, Jul. 1, 2011, pp. 859-863, vol. 46, No. 7.
Zhen-Zhen Yang et al., "Enhanced brain distribution and pharmacodynamics of rivastigmine by liposomes following intranasal administration," International Journal of Pharmaceutics, May 13, 2013, pp. 344-354, vol. 452, No. 1.
Dawn F. Ionescu et al., "Ziprasidone augmentation for anxious depression-", International Clinical Psychopharmacology, Nov. 1, 2016, pp. 341-346, vol. 31, No. 6.
Luciano Roman-Albasini et al., "Antidepressant-relevant behavioral and synaptic molecular effects of long-term fasudil treatment in chronically stressed male rats," Neurobiology of Stress, Nov. 1, 2020, pp. 10,0234-10,0234, No. 13.
Karthik Arumugam et al., "A study of rivastigmine liposomes for delivery into the brain through intranasal route," Acta Pharmaceutica, Sep. 1, 2008, pp. 287-297, vol. 58, No. 3.
Abdulrahman K Al Asmari et al., "Preparation, characterization, and in vivo evaluation of intranasally adminstered liposomal formulation of donepezil," Drug Design, Development and Therapy, Jan. 12, 2016, pp. 205-215, vol. 10.
Office Action for related Europe Application No. 19840670.4, mailed Apr. 4, 2022.
Office Action for related China Application No. 201980049087.2, mailed Jun. 30, 2022.
SIPO Office action dated Dec. 16, 2022 in application No. 201980049087.2.
SIPO Office action dated May 12, 2023 in application No. 201980049087.2.
Taiwan Office action dated Jul. 28, 2021.
Taiwan Office action dated Jul. 28, 2021 (citing CN105163720 and CN103370055).
Surojit Sur, et al., Remote loading of preencapsulated drugs into stealth liposomes, Proc Natl Acad Sci U S A. 2014; 111(6): 2283-2288.
Rebekah K Franklin, et al., A Novel Loading Method for Doxycycline Liposomes for Intracellular Drug Delivery: Characterization of In Vitro and In Vivo Release Kinetics and Efficacy in a J774A.1 Cell Line Model of Mycobacterium smegmatis Infection, Drug Metab Dispos. 2015; 43 (8):1236-45.
Yong Xu et al., Paclitaxel-loaded stealth liposomes: Development, characterization, pharmacokinetics, and biodistribution, Artificial Cells, Nanomedicine, and Biotechnology, 2016; 44: 350-355.

* cited by examiner

SUSTAINED-RELEASE PHARMACEUTICAL COMPOSITIONS COMPRISING A THERAPEUTIC AGENT FOR TREATING DEMENTIA AND USES THEREOF

CROSS-REFERENCE TO RELATED APPLICATIONS

This application claims the benefit of U.S. Application No. 62/702,563, filed on 24 Jul., 2018, the entire disclosure of which is incorporated herein by reference.

TECHNICAL FIELD

The present invention is directed to a sustained-released pharmaceutical composition comprising a therapeutic agent for treating dementia with a high drug to lipid ratio and a high drug encapsulation efficiency using at least one trapping agent. The high drug to lipid ratio, high encapsulation efficiency and sustained release profile of the pharmaceutical composition reduces the frequency of drug administration, increases patient compliance and improves the therapeutic outcome.

BACKGROUND

Rivastigmine, donepezil, galantamine and memantine have been approved for the treatment of dementia associated with Alzheimer's disease and Parkinson's disease in many countries. These medications can be administered orally in tablet, capsule or solution form, or by transdermal patch. However, patient compliance remains low for the once-daily or twice-daily dosing frequency as patients with dementia often forget or resist to take the medicine or have trouble swallowing as the disease progresses. Therefore, it's difficult to ensure patient medication adherence to maintain the circulating drug concentration within the therapeutic window. On the other hand, it is costly to retain a healthcare professional or a care giver to administer the drug, even for once daily administration.

Liposomes as a drug delivery system is a successful technology and has been widely used for developing sustained-released formulations for various drugs. Drug loading into liposomes can be attained either passively (the drug is encapsulated during liposome formation) or remotely/actively (creating a transmembrane pH- or ion-gradient during liposome formation and then the drug is loaded by the driving force generated from the gradients after liposome formation) (U.S. Pat. Nos. 5,192,549 and 5,939,096). Although the general method of drug loading into liposomes is well documented in the literature, only a handful of therapeutic agents were loaded into liposomes with high encapsulation efficiency. Various factors can affect the drug to lipid ratio and encapsulation efficiency of liposomes, including but not limited to, the physical and chemical properties of the therapeutic agent, for example, hydrophilic/hydrophobic characteristics, dissociation constant, solubility and partition coefficient, lipid composition, the choice of the trapping agent or reaction solvent, and particle size (Proc Natl Acad Sci USA. 2014; 111(6): 2283-2288 and Drug Metab Dispos. 2015; 43 (8):1236-45).

Several liposomal formulations of rivastigmine or donepezil have been described but with limitations. Yang et al. discloses a liposomal rivastigmine formulation wherein the liposomes are about 170 nm in diameter and rivastigmine was remotely loaded using ammonium sulfate as a trapping agent. The encapsulation efficiency of this formulation was around 30% with a final drug to lipid ratio (D/L) of 0.15 (Int J Pharm. 2013;452(1-2):344-54). A multilamellar vesicle (MLV) liposomal rivastigmine was obtained using passive loading method but the in vivo study in rats showed the half-life of this MLV liposomal rivastigmine administered via intranasal route was only 109 minutes (Acta Pharm. 2008; 58(3):287-97). A liposomal donepezil formulation prepared by the passive loading method demonstrated that the half-life in rats was prolonged by 1.4-fold compared to free donepezil via intranasal administration (Drug Des Devel Ther. 2016; 10:205-15).

There remains an unmet need for a sustained release formulation with a high drug encapsulation efficiency to reduce dosing frequency for anti-dementia drugs and improve therapeutic outcome. The present invention addresses this need and other needs.

SUMMARY OF THE INVENTION

In one embodiment, sustained release pharmaceutical compositions are provided. The pharmaceutical composition comprises (a) at least one liposome comprising a bilayer membrane, said bilayer membrane includes at least one lipid; (b) a trapping agent; and (c) a therapeutic agent for treating dementia, wherein the molar ratio of the therapeutic agent to the lipid is equal to or higher than 0.2.

According to another embodiment of the present invention, methods are provided for treating dementia, comprising the steps of administering a pharmaceutical composition described herein to a subject in need thereof.

Also provided are the use of the pharmaceutical composition described herein in the manufacture of a medicament for therapeutic and/or prophylactic treatment of dementia.

Further provided is a medicament for treating dementia, comprising a therapeutically effective amount of the pharmaceutical composition described herein.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

A further understanding of the nature and advantages of the present invention may be realized by reference to the remaining portions of the specification and the drawings.

DETAILED DESCRIPTION OF THE INVENTION

Figure 1:
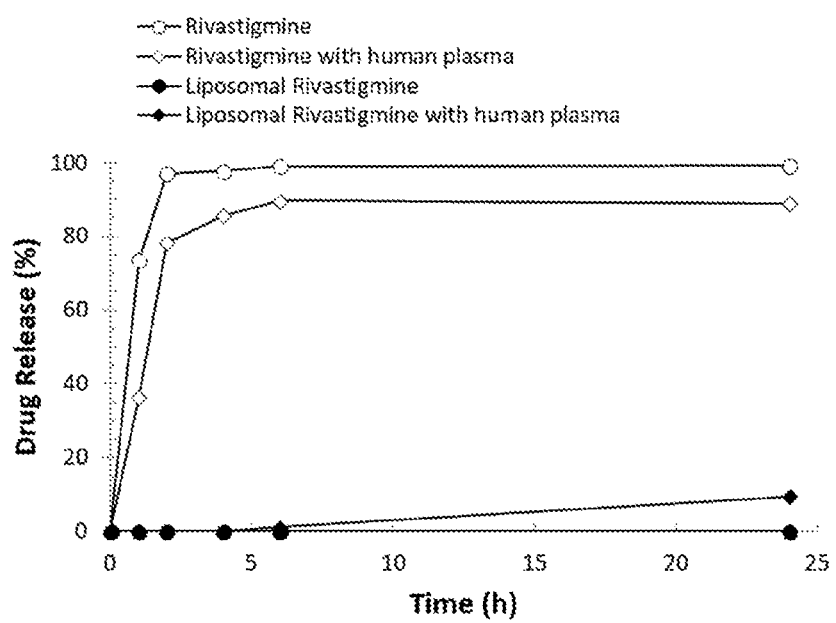
FIG. 1 is a line graph showing the in vitro release profile of liposomal rivastigmine and free rivastigmine.

As employed above and throughout the disclosure, the following terms, unless otherwise herein, the singular forms "a," "an" and "the" include the plural reference unless the context clearly indicates otherwise.

All numbers herein may be understood as modified by "about." As used herein, the term "about" refers to a range of ±10% of a specified value.

An "effective amount" as used herein, refers to a dose of the pharmaceutical composition to reduce the symptoms and signs of dementia, such as memory loss, confusion about time and place, and repetitive behavior, which is detectable clinically, radiologically through various imaging modalities or by examination of specific biomarkers. The term "effective amount" and "therapeutically effective amount" are used interchangeably.

The term "treating," "treated," or "treatment" as used herein includes preventative (e.g. prophylactic), palliative, and curative methods, uses or results. The terms "treatment" or "treatments" can also refer to compositions or medicaments. Throughout this application, by treating is meant a method of reducing or delaying one or more symptoms or signs of dementia or the complete amelioration of dementia as detected by art-known techniques, which include, but are not limited to, clinical examination, imaging or cerebrospinal fluid (CSF) biomarkers (for example, detection of low CSF amyloid $\beta_{3-42}$ and high CSF total-tau or phospho-tau). For example, a disclosed method is considered to be a treatment if there is about a 0.1% reduction in one or more symptoms of dementia in a subject when compared to the subject prior to treatment or control subjects. Thus, the reduction can be about a 0.1, 1, 5, 10, 20, 30, 40, 50, 60, 70, 80, 90, 100%, or any amount of reduction in between.

The term "dementia" as used herein, encompasses a variety of types and subtypes of dementia of various etiologies and causes, either known or unknown, including, but not limited to, Parkinson's disease, Alzheimer's disease and vascular dementia.

The term "subject" can refer to a vertebrate having or at risk of developing dementia or to a vertebrate deemed to be in need of dementia treatment. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Liposome

The terms "liposome," "liposomal" and related terms as used herein are characterized by an interior aqueous space sequestered from an outer medium by one or more bilayer membranes forming a vesicle. In certain embodiments, the interior aqueous space of the liposome is substantially free of a neutral lipid, such as triglyceride, non-aqueous phase (oil phase), water-oil emulsions, a second liposome or other mixtures containing non-aqueous phase. Non-limiting examples of liposomes include small unilamellar vesicles (SUV), large unilamellar vesicles (LUV), and multi-lamellar vesicles (MLV) with an average diameter ranges from 50-500 nm, 50-450 nm, 50-400 nm, 50-350 nm, 50-300 nm, 50-250 nm, 50-200 nm, 100-500 nm, 100-450 nm, 100-400 nm, 100-350 nm, 100-300 nm, 100-250 nm or 100-200 nm, all of which are capable of passing through sterile filters.

Bilayer membranes of liposomes are typically formed by at least one lipid, i.e. amphiphilic molecules of synthetic or natural origin that comprise spatially separated hydrophobic and hydrophilic domains. Examples of lipid, including but not limited to, dialiphatic chain lipids, such as phospholipids, diglycerides, dialiphatic glycolipids, single lipids such as sphingomyelin and glycosphingolipid, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanolamine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanolamine (PEG-DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). In some embodiments, the lipid is a lipid mixture of one or more of the foregoing lipids, or mixtures of one or more of the foregoing lipids with one or more other lipids not listed above, membrane stabilizers or antioxidants.

In some embodiments, the mole percent of the lipid in the bilayer membrane is equal or less than about 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45 or any value or range of values therebetween (e.g., about 45-85%, about 45-80%, about 45-75%, about 45-70%, about 45-65%, about 50-85%, about 50-80%, about 50-75%, about 50-70%, or about 50-65%).

In some embodiments, the lipid of the bilayer membrane comprises a mixture of a first lipid and a second lipid. In some embodiments, the first lipid is selected from the group consisting essentially of phosphatidylcholine (PC), HSPC, DSPC, DPPC, DMPC, PSPC and a combination thereof and the second lipid is selected from the group consisting essentially of a phosphatidylethanolamine, phosphatidylglycerol, PEG-DSPE, DPPG and a combination thereof. In other embodiments, the mole percent of the first lipid in the bilayer membrane is equal or less than about 84.9, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30 or any value or range of values therebetween (e.g., about 30-84.9%, about 30-80, about 35-75, about 40-70, about 30-70, about 30-60, about 35-84.9%, about 35-80, about 35-70, about 35-60, about 40-84.9%, about 40-80, about 40-75 or about 40-62) and the mole percent of the second lipid in the bilayer membrane is equal to or less than about 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 to 0.1 or any value or range of values therebetween (e.g., about 0.1-30%, about 0.1-25%, about 0.1-23%, about 0.5-30%, about 0.5-25%, about 0.5-23%, about 0.7-30%, about 0.7-25% or about 0.7-23%).

Bilayer membranes of liposomes further comprise less than about 55 mole percentage of steroids, preferably cholesterol. In certain embodiments, the % of cholesterol in the bilayer membrane is about 15-55%, about 20-55, about 25-55%, about 20-50%, about 25-50%, about 15-45%, about 20-45%, about 25-45%, about 15-40%, about 20-40%, about 25-40%, about 15-35%, about 20-35% or about 25-35%. In one exemplary embodiment, the mole % of the lipid and cholesterol in the bilayer membrane is about 50-80%: 20-50%, 45-75%: 25-55% or 45-85%:15-55%. In another exemplary embodiment, the mole % of the first lipid, the second lipid and cholesterol in the bilayer membrane is about 30-84.9%: 0.1%-30%: 15-55%, 45-80: 0.1-30%: 20-50%, 50-75%: 0.1-25%: 20-45% or 50-95%: 0.1-25%: 10-50%.

Remote Loading

The term "remote loading" as used herein is a drug loading method which involves a procedure to transfer drugs from the external medium across the bilayer membrane of the liposome to the interior aqueous space by a polyatomic ion-gradient. Such gradient is generated by encapsulating at least one polyatomic ion as a trapping agent in the interior aqueous space of the liposome and replacing the outer medium of the liposome with an external medium, for example, pure water, sucrose solution or saline with a lower polyatomic ion concentration by known techniques, such as column separation, dialysis or centrifugation. A polyatomic ion gradient is created between the interior aqueous space and the external medium of the liposomes to trap the therapeutic agent in the interior aqueous space of the liposomes. Exemplary polyatomic ion as trapping agents include, but are not limited to, sulfate, sulfite, phosphate, hydrogen phosphate, molybdate, carbonate and nitrate. Exemplary trapping agents include, but are not limited to, ammonium sulfate, ammonium phosphate, ammonium molybdate, ammonium sucrose octasulfate, triethylammonium sucrose octasulfate, dextran sulfate, or a combination thereof.

In an embodiment, the concentration of triethylammonium sucrose octasulfate is about 10 to 200 mM or about 50 to about 150 mM. In another embodiment, the concentration of ammonium sulfate is about 100 to about 600 mM, about 150 to about 500 mM or about 200 to about 400 mM. In yet another embodiment, the concentration of ammonium phosphate is about 100 to about 600 mM, about 150 to about 500 mM or about 200 to about 400 mM. In yet another embodiment, the concentration of dextran sulfate is about 0.1 to 10 mM, about 0.1 to 5 mM or about 0.1 to 1 mM.

In accordance with the invention, the liposome encapsulating a trapping agent can be prepared by any of the techniques now known or subsequently developed. For example, the MLV liposomes can be directly formed by a hydrated lipid film, spray-dried powder or lyophilized cake of selected lipid compositions with trapping agent; the SUV liposomes and LUV liposomes can be sized from MLV liposomes by sonication, homogenization, microfluidization or extrusion.

Pharmaceutical Compositions

The present invention is directed to a sustained release pharmaceutical composition, comprising (a) at least one liposome comprising bilayer membrane; (b) a trapping agent; and (c) a therapeutic agent for treating dementia, wherein the bilayer membrane comprises at least one lipid and the molar ratio of the therapeutic agent to the lipid is above or equal to 0.2. In some embodiments, the molar ratio of the therapeutic agent to the lipid is above or equal to 0.2 to less than about 20, less than about 15, less than about 10, less than about 5.

In one embodiment, the sustained release pharmaceutical composition further comprises at least one pharmaceutically acceptable excipient, diluent, vehicle, carrier, medium for the active ingredient, a preservative, cryoprotectant or a combination thereof. In one exemplary embodiment, the weight percent of the bilayer membrane in the pharmaceutical composition is about 0.1-15%; the weight percent of the trapping agent in the pharmaceutical composition is about 0.1-12%; and the weight percent of the pharmaceutically acceptable excipient (such as sucrose, histidine, sodium chloride and ultrapure water), diluent, vehicle, carrier, medium for the active ingredient, a preservative, cryoprotectant or a combination thereof in the pharmaceutical composition is about 75.0-99.9%.

In certain embodiments, the therapeutic agent for treating dementia or the anti-dementia drug is an acetylcholinesterase inhibitor or memantine. In an exemplary embodiment, the acetylcholinesterase inhibitor is selected from the group consisting of rivastigmine, donepezil, galantamine and a combination thereof. In another embodiment, the therapeutic agent for treating dementia or anti-dementia drug is memantine and the trapping agent is triethylammonium sucrose octasulfate. The sustained release profile of the pharmaceutical composition prolongs the half-life of the anti-dementia drug and maintains the therapeutic plasma concentration of the anti-dementia drug for a longer period of time, hence, sustains the therapeutic effect and reduces the frequency of drug administration.

In one aspect, the sustained release profile of the pharmaceutical composition is due to a high drug encapsulation efficiency. The encapsulation efficiency of the pharmaceutical composition is at least 50%, 55%, 60%, 65%, 70%, 75% or 80%.

In another aspect, sustained release profile of the pharmaceutical composition is due to the higher drug to lipid molar ratio. In an exemplary embodiment, the molar ratio of the therapeutic agent for treating dementia to the one or more lipid is above or equal to about 0.20, 0.21, 0.22, 0.23, 0.24 or 0.25, alternatively from about 0.2 to 10, from about 0.2 to 5, from about 0.2 to 2 or from about 0.2 to 1.

In yet another aspect, the half-life of the therapeutic agent for treating dementia in the pharmaceutical composition described herein is extended by at least 2-fold, at least 5-fold, at least 7.5-fold, at least 10-fold or at least 20-fold compared to that of the free therapeutic agent for treating dementia.

The invention also provides methods of treating dementia, comprising the administration of an effective amount of the pharmaceutical composition described herein to a subject in need thereof, whereby the symptoms and/or signs of the dementia in the subject are reduced.

The pharmaceutical composition is formulated to be suitable for cutaneous administration, such as subcutaneous, subdermal, intradermal, transdermal or intramuscular route. The pharmaceutical composition is also formulated to be administered as a transdermal patch.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, any existing medical conditions, and on the discretion of medical professionals.

In one embodiment, the pharmaceutical compositions disclosed herein display a significant sustained-release profile of the therapeutic agent. For example, the pharmaceutical composition of the present invention extended the half-life of subcutaneous administered rivastigmine to 15.8 hours in rats (as disclosed in Example 4) compared to either the FDA approved rivastigmine formulation via oral administration (0.4 hour, Exelon Capsules New Drug Application submitted package, Novartis Pharmaceuticals Corporation, Application No.: 020823) or a published liposomal rivastigmine formulation via intranasal administration (1.8 hours, Acta Pharm. 2008; 58(3):287-97) in rats. In another example, the pharmaceutical composition disclosed herein extended the half-life of subcutaneous administered donepezil to 34.3 hours in rats (as described in Example 5) compared the half-life of either free donepezil via oral (4.3 hours) and intranasal administration (4.2 hours) or liposomal donepezil formulation via intranasal administration (5.8 hours) reported in the literature (Drug Des Devel Ther. 2016; 10:205-15). These pharmaceutical compositions are developed to reduce the dosing frequency from twice-daily to daily, once every two days, once every three days, once every five days, once every six days, weekly, once every two weeks, once a month, once every two months, once every three months, once every four months, once every five months or once every six months.

Examples

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated.

Example 1. Preparation of Liposomal Rivastigmine Formulation

Empty liposomes were prepared by a lipid film hydration-extrusion method. HSPC, cholesterol, and DSPE-PEG2000 (mole percent 59.5/39.6/0.9) were dissolved in chloroform and a thin lipid film was formed by removing the organic solvent under vacuum in a rotary evaporator. The dry lipid film was hydrated in 75 mM triethylammonium sucrose octasulfate (pH 6.0) at 60° C. for 30 min and liposomes were formed with triethylammonium sucrose octasulfate encapsulated in the aqueous core. After six freeze-thaw cycles between liquid nitrogen and water at 60° C., the liposomes were subsequently extruded ten times through polycarbonate filter membranes with a pore size of 0.2 m. Unencapsulated triethylammonium sucrose octasulfate was removed by dialysis against a 9.4% sucrose solution.

A reaction mixture containing 2.0 mg/mL of rivastigmine tartrate (Cayman Chemical Company, US), empty liposomes (with 20.0 mM of lipids) prepared according to the preceding paragraph, and 10 mM histidine buffer (pH 6.5) was incubated at 60° C. for 30 min. The unencapsulated rivastigmine tartrate of the reaction mixture was separated by a Sephadex™ G-50 Fine gel (GE Healthcare) or dialysis bag (Spectrum Labs) against a 9.4% sucrose solution to obtain liposomal rivastigmine formulation. Encapsulated rivastigmine tartrate concentrations and the lipid concentrations of the liposomal rivastigmine formulation were measured using an ultraviolet/visible (UV/Vis) spectrophotometer to calculate the drug to lipid molar ratio (D/L) of the liposomal rivastigmine formulation.

The encapsulation efficiency was calculated by the drug to lipid molar ratio (D/L) of the liposomal rivastigmine formulation compared to that of the nominal D/L of the reaction mixture, which was calculated by dividing the concentration of rivastigmine tartrate by the lipid concentration of the empty liposome. The particle size distribution was measured by a dynamic light scattering instrument (Zetasizer Nano-ZS90, Malvern).

Using 75 mM triethylammonium sucrose octasulfate as a trapping agent, the liposomal rivastigmine formulation has a final D/L of 0.24, an encapsulation efficiency of 96.8%, and the mean diameter of the liposomes was 193.7 nm.

Example 2. Preparation of Liposomal Donepezil Formulation

Empty liposomes were prepared according to Example 1. The dry lipid film was hydrated in 300 mM ammonium sulfate solution at 60° C. for 30 minutes and liposomes were formed with ammonium sulfate encapsulated in the aqueous core. After six freeze-thaw cycles between liquid nitrogen and water at 60° C., the liposomes were subsequently extruded ten times through polycarbonate filter membranes with a pore size of 0.2 μm. Unencapsulated ammonium sulfate was removed by dialysis against a 9.4% sucrose solution to create a sulfate gradient between inner aqueous phase and outer aqueous phase of liposomes.

A reaction mixture containing 2.5 mg/mL of donepezil hydrochloride (MedChem Express) and empty liposomes (with 16.7 mM of lipids) prepared according to the preceding paragraph was incubated at 60° C. for 30 min. The unencapsulated donepezil hydrochloride was separated by a Sephadex™ G-50 Fine gel (GE Healthcare) or dialysis bag (Spectrum Labs) against a 9.4% sucrose solution to obtain liposomal donepezil formulation. The D/L and encapsulation efficiency of liposomal donepezil formulation were calculated according to Example 1.

Using 300 mM ammonium sulfate as a trapping agent, the liposomal donepezil formulation has a final D/L of 0.28 and an encapsulation efficiency of 79.4%. The mean particle size of the liposomes was 191.1 nm.

Example 3. The Effect of Different Trapping Agents on Drug Loading Profile

The liposome formulations were prepared according to Example 1, with the following trapping agents: (1) 75 mM of triethyl ammonium sucrose octasulfate, (2) 300 mM of ammonium sulfate, (3) a mixture of 300 mM of ammonium sulfate and 0.3 mM of dextran sulfate, (4) 200 mM ammonium phosphate and (5) 250 mM of ammonium sulfate. Table 1 shows the effect of different trapping agents on drug loading.

the dialysis bags were sealed. Each dialysis bag was immersed in 25 mL PBS at pH 7.4 in a 50-mL centrifuge tube and incubated in a water bath at 37±1° C. for 24 hours. At designated time points after incubation (1, 2, 4, 6 and 24 hours), 0.5 mL aliquot from the 25-mL PBS was sampled and 0.5 mL of fresh PBS was added to replace the sampling

TABLE 1

The drug loading profile of different trapping agents

| Composition | Bilayer membranes (mole percent) | Compound | Trapping Agent | Purified D/L (mole/mole) | Average Particle Size (nm) |
|---|---|---|---|---|---|
| 1 | HSPC/cholesterol/DSPE-PEG2000 (59.5/39.6/0.9) | Rivastigmine | 1 | 0.54 | n.d. |
| 2 | HSPC/cholesterol/DSPE-PEG2000 (59.5/39.6/0.9) | Rivastigmine | 1 | 0.24 | 193.7 |
| 3 | HSPC/cholesterol (60/40) | Rivastigmine | 1 | 0.47 | 202.0 |
| 4 | HSPC/cholesterol/DPPG (59.5/39.6/0.9) | Rivastigmine | 2 | 0.28 | 212.1 |
| 5 | HSPC/cholesterol/DSPE-PEG2000 (59.5/39.6/0.9) | Rivastigmine | 3 | 0.30 | n.d. |
| 6 | HSPC/cholesterol/DSPE-PEG2000 (59.5/39.6/0.9) | Donepezil | 1 | 0.69 | n.d. |
| 7 | HSPC/cholesterol/DSPE-PEG2000 (43.5/34.5/22) | Donepezil | 1 | 0.32 | 211.1 |
| 8 | HSPC/cholesterol/DSPE-PEG2000 (59.5/39.6/0.9) | Donepezil | 2 | 0.28 | 191.1 |
| 9 | DMPC/cholesterol/DSPE-PEG2000 (59.5/40/0.5) | Donepezil | 2 | 0.66 | 180.8 |
| 10 | HSPC/cholesterol/DPPG (59.5/39.6/0.9) | Donepezil | 2 | 0.74 | 206.7 |
| 11 | DPPC/cholesterol/DSPE-PEG2000 (59.5/39.6/0.9) | Donepezil | 4 | 0.28 | 183.3 |
| 12 | HSPC/cholesterol/DSPE-PEG2000 (59.5/39.6/0.9) | Galantamine | 1 | 1.01 | n.d. |
| 13 | HSPC/cholesterol/DSPE-PEG2000 (59.5/39.6/0.9) | Galantamine | 3 | 0.28 | n.d. |
| 14 | DPPC/cholesterol/DSPE-PEG2000 (57.6/37.1/5.3) | Galantamine | 4 | 0.21 | 187.0 |
| 15 | HSPC/cholesterol/DSPE-PEG2000 (58.3/38.8/2.9) | Galantamine | 5 | 0.23 | n.d. |
| 16 | HSPC/cholesterol/DSPE-PEG2000 (59.5/39.6/0.9) | Memantine | 1 | 0.42 | n.d. |
| 17 | HSPC/cholesterol/DSPE-PEG2000 (59.5/39.6/0.9) | Memantine | 2 | 0.23 | n.d. |

The encapsulation efficiencies of the compositions in Table 1 are as follows: Composition 1: 71.9%, Composition 2: 96.8%, Composition 3: 62.3%, Composition 4: 55.8%, Composition 5: 59.2%, Composition 6: 57.6%, Composition 7: 89.3%, Composition 8: 79.4%, Composition 9: 91.9%, Composition 10: >99%, Composition 11: 78.6%, Composition 12: 62.2%, Composition 13: 67.9%, Composition 14: 49.5%, Composition 15: 56.8%, and Composition 16: 60.2%

Example 4. Prolonged Release Profile of Liposomal Rivastigmine

Two in vitro release systems were used in this study, the first system was the plasma free environment and the second system was the human plasma environment. To set up the first in vitro release system, 1.0 mL of liposomal rivastigmine formulation prepared according to Example 1 and 1.0 mL of free rivastigmine tartrate were placed in separate dialysis bags (Spectra/Pro*6 dialysis membrane, MWCO 50 kDa, Spectrum Labs) and both ends of the dialysis bags were sealed. To set up the second in vitro release system, 1.0 mL of liposomal rivastigmine formulation prepared according to Example 1 and 1.0 mL of free rivastigmine tartrate were placed in separate dialysis bags, each containing 1 mL of human plasma (Valley Biomedical, Inc.) and both ends of aliquot. Drug concentrations of the sampling aliquots at each time point were analyzed using high performance liquid chromatography (HPLC) to create the in vitro release profile.

Referring to FIG. 1, in the first in vitro plasma free release system, almost one hundred percent of rivastigmine was released from the free rivastigmine formulation through the dialysis bag within 2 hours of adding the formulation, whereas less than 1% of the rivastigmine in the liposomal rivastigmine formulation was released through the dialysis bag over a 24-hour period.

In the second in vitro human plasma release system, 90% of rivastigmine was released from the free rivastigmine formulation within 4 hours of adding the formulation, whereas only 10% of the rivastigmine was released from the liposomal rivastigmine formulation over a 24-hour period.

Example 5. Pharmacokinetics (PK) Study of Liposomal Rivastigmine

An in vivo PK evaluation of the liposomal rivastigmine formulation was performed using 7-8 weeks old female Sprague-Dawley rats. The rats were housed in a holding room which operated on a 12-hr light/12-hr dark circadian cycle with free access to water and food.

The rats were divided into two groups (n=3 in each group), one group received subcutaneous injection of 10 mg/kg of free rivastigmine tartrate, prepared by dissolving rivastigmine tartrate in ultrapure water with a final concentration of 2 mg/mL. The other group received subcutaneous injection of 10 mg/kg of liposomal rivastigmine tartrate, prepared according to Example 1. Blood samples were collected at 15 min, 1, 2, 4, 6, 8, 24, 48, and 72 hours post-injection. Plasma samples were obtained by centrifugation, kept frozen at −80° C. and analyzed using a non-compartmental analysis model in PKSolver (Comput Methods Programs Biomed. 2010; 99(3):306-314). The PK parameters of the two rivastigmine formulations are summarized in Table 2.

The results in Table 2 show the $C_{max}$ of liposomal rivastigmine group was 8.1% of that of free rivastigmine group, and the half-life ($t_{1/2}$) of liposomal rivastigmine was significantly longer compared to that of the free rivastigmine group. The area under the curve ($AUC_{0-t}$) of liposomal rivastigmine indicates 90.2% of rivastigmine was released from the liposomal rivastigmine formulation 72 hours post-injection compared to the $AUC_{0-t}$ of free rivastigmine, which indicates 100% of rivastigmine was released 72 hours post-injection.

TABLE 2

PK parameters derived from rats after single subcutaneous injection of free rivastigmine and liposomal rivastigmine

| Parameters | Unit | Free Rivastigmine | Liposomal Rivastigmine |
| --- | --- | --- | --- |
| $t_{1/2}$ | h | 0.93 | 15.8 |
| $C_{max}$ | ng/mL | 427.3 | 34.7 |
| $AUC_{0-t}$ | h × ng/mL | 896.4 | 809.0 |
| $AUC_{0-inf}$ | h × ng/mL | 898.7 | 855.0 |

Figure 2:
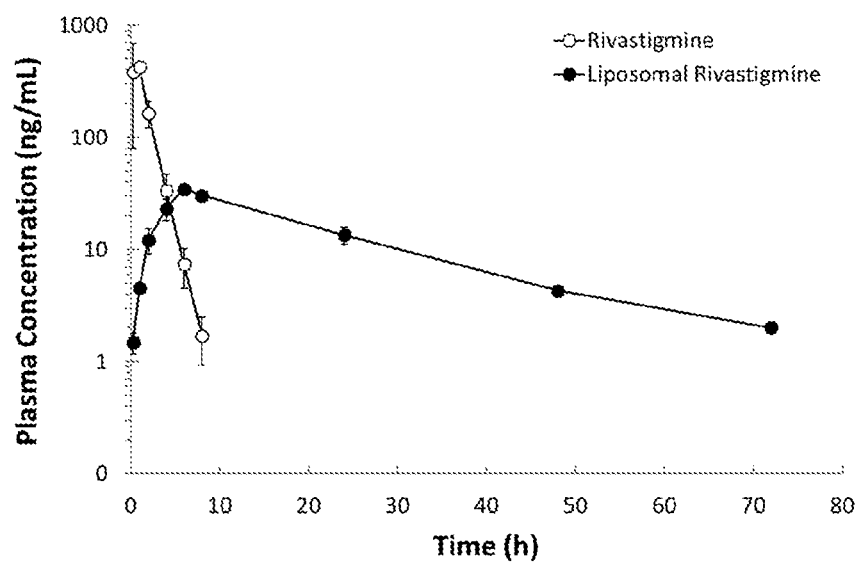
FIG. 2 is a line graph showing the plasma rivastigmine concentration in rats after subcutaneous injection of liposomal rivastigmine and free rivastigmine.

In addition, FIG. 2 shows rivastigmine was undetectable in the plasma of rats 8 hours post free rivastigmine injection whereas rivastigmine was detected in the plasma of rats receiving liposomal rivastigmine formulation up to 72 hours post drug injection. The results support a conclusion that the claimed pharmaceutical composition sustained the release of rivastigmine.

Example 6. Pharmacokinetic Study of Liposomal Donepezil

An in vivo PK evaluation of the liposomal donepezil formulation was performed according to the method of Example 5.

The rats were divided into two groups (n=3 in each group), one group received subcutaneous injection of 10 mg/kg of free donepezil hydrochloride, prepared by dissolving donepezil hydrochloride in ultrapure water with a final concentration of 2.5 mg/mL. The other group received subcutaneous injection of 10 mg/kg of liposomal donepezil hydrochloride, prepared according to Example 2. Blood samples were collected at 15 minutes, 1, 2, 4, 8, 24, 48, 72, 96, and 168 hours post-injection. The PK parameters of the two donepezil formulations are summarized in Table 3.

The results in Table 3 show the $C_{max}$ of liposomal donepezil group was 5.7% of that of free donepezil group, and the $t_{1/2}$ of liposomal donepezil was 10 times longer compared to that of the free donepezil group. The $AUC_{0-t}$ of liposomal donepezil indicates 64.4% of donepezil was released from the liposomal donepezil formulation 168 hours post-injection compared to the $AUC_{0-t}$ of free donepezil, which indicates 100% of donepezil was released 168 hours post-injection.

TABLE 3

PK parameters derived from rats after a single subcutaneous injection of free donepezil and liposomal donepezil

| Parameters | Unit | Free Donepezil | Liposomal Donepezil |
| --- | --- | --- | --- |
| $t_{1/2}$ | h | 3.37 | 34.3 |
| $C_{max}$ | ng/mL | 457 | 26.2 |
| $AUC_{0-t}$ | h × ng/mL | 2571 | 1656 |
| $AUC_{0-inf}$ | h × ng/mL | 2591 | 1722 |

Figure 3:
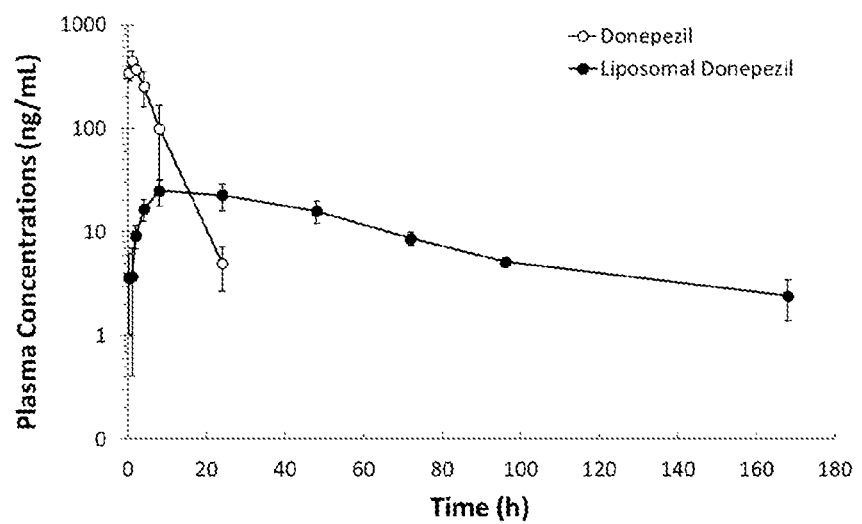
FIG. 3 is a line graph showing the plasma donepezil concentration in rats after subcutaneous injection of liposomal donepezil and free donepezil.

In addition, FIG. 3 shows donepezil was undetectable in the plasma of rats receiving free donepezil injection 24 hours post drug injection whereas donepezil was detected in the plasma of rats receiving liposomal donepezil up to 168 hours post drug injection. The results support a conclusion that the claimed pharmaceutical composition sustained the release of donepezil.

The invention claimed is:

1. A pharmaceutical composition, comprising:
   (a) at least one liposome comprising a bilayer membrane, said bilayer membrane comprises about 40 to about 80 mole % of a first lipid that is selected from the group consisting of phosphatidylcholine (PC), 1,2-distearoyl-sn-glycero-3-phosphocholine (HSPC), 1,2-distearoyl-sn-glycero-3-phosphocholine (DSPC), 1,2-dipalmitoyl-sn-glycero-3-phosphocholine (DPPC), 1,2-dimyristoyl-sn-glycero-3-phosphocholine (DMPC), 1-palmitoyl-2-stearoyl-sn-glycero-3-phosphocholine (PSPC) and any combination thereof, about 20 to about 40% mole % of cholesterol and optionally 0.1-30% mole % of a second lipid that is selected from the group consisting of a phosphatidylethanolamine, phosphatidylglycerol, N-(carbonyl-methoxypolyethyleneglycol)-1,2-distearoyl-sn-glycero-3-phosphoethanolamine (PEG-DSPE), 1,2-dipalmitoyl-sn-glycero-3-phospho-(1'-rac-glycerol) (DPPG) and any combination thereof;
   (b) a trapping agent that is selected from the group consisting of about 10 to 200 mM triethylammonium sucrose octasulfate, about 100 to 600 mM ammonium sulfate, about 0.1 to 10 mM dextran sulfate and any combination thereof; and
   (c) a therapeutic agent that is an acetylcholinesterase inhibitor or memantine,
   wherein the molar ratio of the therapeutic agent to the lipid is equal to or higher about than 0.2 and the therapeutic agent is encapsulated in the liposome with an encapsulation efficiency higher than about 50%.

2. The pharmaceutical composition of claim 1, wherein the mean particle size of the liposome is from about 50 nm to 500 nm.

3. The pharmaceutical composition of claim 1, wherein the molar ratio of the therapeutic agent to the lipid is equal to or higher about than 0.42.

4. The pharmaceutical composition of claim 3, wherein the first lipid is HSPC, the optionally second lipid is DSPE-PEG2000, the trapping agent is triethylammonium sucrose octasulfate and the therapeutic agent is rivastigmine.

5. The pharmaceutical composition of claim 3, wherein the first lipid is HSPC, the optionally second lipid is 0.5-20 mole % of DSPE-PEG2000, the trapping agent is triethylammonium sucrose octasulfate and the therapeutic agent is donepezil.

6. The pharmaceutical composition of claim 3, wherein the first lipid is HSPC, and the second lipid is DPPG or the first lipid is DMPC and the second lipid is DSPE-PEG2000, the trapping agent is ammonium sulfate and the therapeutic agent is donepezil.

7. The pharmaceutical composition of claim 3, wherein the first lipid is HSPC, the second lipid is DSPE-PEG2000, the trapping agent is triethylammonium sucrose octasulfate and the therapeutic agent is galantamine.

8. The pharmaceutical composition of claim 3, wherein the first lipid is HSPC, the second lipid is DSPE-PEG2000, the trapping agent is triethylammonium sucrose octasulfate and the therapeutic agent is memantine.

9. The pharmaceutical composition of claim 1, wherein the acetylcholinesterase inhibitor is selected from the group consisting of rivastigmine, donepezil, galantamine and a combination thereof.

10. A method of treating dementia, comprising:
administering a pharmaceutical composition of claim 1 to a subject in need thereof.

11. The method of claim 10, wherein the half-life of the therapeutic agent in the pharmaceutical composition is extended by at least 2-fold, at least 5-fold, at least 7.5-fold, at least 10-fold, or at least 20-fold compared to that of the free therapeutic agent.

12. The method of claim 10, wherein the pharmaceutical composition is administered at least once every three days, at least once every week, at least once every two weeks or at least once a month.

13. The method of claim 10, wherein the pharmaceutical composition is administered by cutaneous injection.

14. The method of claim 13, wherein the cutaneous injection includes subcutaneous, subdermal, intradermal, transdermal or intramuscular route.

15. The pharmaceutical composition of claim 1, wherein the first phospholipid is HSPC, DMPC, DPPC or any combination thereof and the second phospholipid is PEG-DSPE, DPPG or any combination thereof.

\* \* \* \* \*